(12) United States Patent
Wolf et al.

(10) Patent No.: US 8,609,088 B2
(45) Date of Patent: Dec. 17, 2013

(54) INTRANASAL DELIVERY OF THERAPEUTIC ENZYMES TO THE CENTRAL NERVOUS SYSTEM FOR THE TREATMENT OF LYSOSOMAL STORAGE DISEASES

(75) Inventors: Daniel A. Wolf, Lund (SE); William H. Frey, II, White Bear Lake, MN (US); R. Scott McIvor, St. Louis Park, MN (US); Leah R. Hanson, Vadnais Heights, MN (US)

(73) Assignees: Regents of the University of Minnesota, St. Paul, MN (US); HealthPartners Research & Education, Bloomington, MN (US)

( * ) Notice: Subject to any disclaimer, the term of this patent is extended or adjusted under 35 U.S.C. 154(b) by 0 days.

(21) Appl. No.: 13/465,575

(22) Filed: May 7, 2012

(65) Prior Publication Data

US 2012/0288489 A1 Nov. 15, 2012

Related U.S. Application Data

(60) Provisional application No. 61/484,378, filed on May 10, 2011.

(51) Int. Cl.
*A61K 38/46* (2006.01)
(52) U.S. Cl.
USPC ....................................................... 424/94.61
(58) Field of Classification Search
None
See application file for complete search history.

(56) References Cited

U.S. PATENT DOCUMENTS 6,858,206 B2 * 2/2005 Kakkis .......................... 424/94.1
2009/0136505 A1 5/2009 Bentz et al.

FOREIGN PATENT DOCUMENTS

WO WO-2008049588 A1 5/2008

OTHER PUBLICATIONS

Kakkis et al., "Intrathecal enzyme replacement therapy reduces lysosomal storage in the brain and meninges of the canine model of MPS I" (2004) Molecular Genetics and Metabolism, vol. 83, 163-174.*
Donovan & Huang, "Large molecule and particulate uptake in the nasal cavity: the effect of size on nasal absorption." (1998) Advanced Drug Delivery Reviews, vol. 29, 147-155.*
Talegaonkar & Mishra, "Intranasal delivery; an approach to bypass the blood brain barrier." (2004) Indian Journal of Pharmacology, vol. 36, 140-147.*
Zheng et al., "Treatment of the mouse model of mucopolysaccharidosis I with retrovirally transduced bone marrow" (2003) Molecular Genetics and Metabolism, vol. 79, 233-244.*
Dhuria, S. V, et al., "Intranasal delivery to the central nervous system: mechanisms and experimental considerations", J Pharm Sci., 99(4), (Apr. 2010), 1654-73.

* cited by examiner

*Primary Examiner* — Ralph Gitomer
*Assistant Examiner* — Teresa E Knight
(74) *Attorney, Agent, or Firm* — Schwegman, Lundberg & Woessner, P.A.

(57) ABSTRACT

The invention provides a method to prevent, inhibit or treat one or more neurological symptoms associated with a lysosomal storage disease in a mammal in need thereof, which includes intranasally administering to the mammal a composition comprising an effective amount of a lysosomal storage enzyme or a recombinant adeno-associated virus vector comprising an open reading frame encoding a lysosomal storage enzyme. Also provided are compositions and devices useful in the methods.

17 Claims, 5 Drawing Sheets

INTRANASAL DELIVERY OF THERAPEUTIC ENZYMES TO THE CENTRAL NERVOUS SYSTEM FOR THE TREATMENT OF LYSOSOMAL STORAGE DISEASES

CROSS-REFERENCE TO RELATED APPLICATIONS

This application claims the benefit of the filing date of U.S. application Ser. No. 61/484,378, filed on May 10, 2011, the disclosure of which is incorporated by reference herein.

BACKGROUND

The mucopolysaccharidoses (MPSs) are a group of 11 storage diseases caused by disruptions in glycosaminoglycan (GAG) catabolism, leading to their accumulation in lysosomes (Muenzer, 2004; Munoz-Rojas et al., 2008). Manifestations of varying severity include organomegaly, skeletal dysplasias, cardiac and pulmonary obstruction and neurological deterioration. For MPS I, deficiency of iduronidase (IDUA), severity ranges from mild (Scheie syndrome) to moderate (Hurler-Scheie) to severe (Hurler syndrome), with the latter resulting in neurologic deficiency and death by age 15 (Muenzer, 2004; Munoz-Rojas et al., 2008). Therapies for MPSs have been for the most part palliative. However, there are some of the MPS diseases, including Hurler syndrome, for which allogeneic hematopoietic stem cell transplantation (HSCT) has exhibited efficacy (Krivit, 2004; Orchard et al., 2007; Peters et al., 2003). Additionally, for more and more of the MPS diseases, enzyme replacement therapy (ERT) is becoming available (Brady, 2006). In general, HSCT and ERT result in the clearing of storage materials and improved peripheral conditions, although some problems persist after treatment (skeletal, cardiac, corneal clouding). The primary challenge in these cellular and enzyme therapies is effectiveness in addressing neurological manifestations, as peripherally administered enzyme does not penetrate the blood-brain barrier and HSCT has been found to be of benefit for some, but not all, MPS's.

MPS I has been one of the most extensively studied of the MPS diseases for development of cellular and molecular therapies. The effectiveness of allogeneic HSCT is most likely the result of metabolic cross-correction, whereby the missing enzyme is released from donor-derived cells and subsequently taken up by host cells and trafficked to lysosomes, where the enzyme contributes to lysosomal metabolism (Fratantoni et al., 1968). Clearing of GAG storage materials is subsequently observed in peripheral organs such as liver and spleen, there is relief from cardiopulmonary obstruction and improvement in corneal clouding (Orchard et al., 2007). Of particular importance is the effect of allogeneic stem cell transplantation on the emergence of neurologic manifestations in the MPS diseases. In this regard, there is evidence for several MPS diseases that individuals engrafted with allogeneic stem cells face an improved outcome in comparison with untransplanted patients (Bjoraker et al., 2006; Krivit, 2004; Orchard et al., 2007; Peters et al., 2003). A central hypothesis explaining the neurologic benefit of allogeneic hematopoietic stem cell transplant is the penetration of donor-derived hematopoietic cells (most likely microglia) (Hess et al., 2004; Unger et al., 1993) into the central nervous system, where the missing enzyme is expressed by engrafted cells from which point the enzyme diffuses into CNS tissues and participates in clearing of storage materials. The level of enzyme provided to CNS tissues is thus limited to that amount expressed and released from donor-derived cells engrafting in the brain. While such engraftment is of great benefit for MPS I, recipients nonetheless continue to exhibit below normal IQ and impaired neurocognitive capability (Ziegler and Shapiro, 2007).

The phenomenon of metabolic cross correction also explains the effectiveness of ERT for several lysosomal storage diseases (Brady, 2006), most notably MPS I. However, due to the requirement for penetration of the blood-brain barrier (BBB) by the enzyme missing in the particular lysosomal storage disease (LSD) in order to effectively reach the CNS, effectiveness of enzyme therapy for neurologic manifestations of lysosomal storage disease (LSD) has not been observed (Brady, 2006). Enzymes are almost always too large and generally too charged to effectively cross the BBB. This has prompted investigations into invasive intrathecal enzyme administration (Dickson et al., 2007), for which effectiveness has been demonstrated in a canine model of MPS I (Kakkis et al., 2004) and for which human clinical trials are beginning for MPS I (Pastores, 2008; Munoz-Rojas et al., 2008). Key disadvantages of enzyme therapy include its great expense (>$200,000 per year) and the requirement for repeated infusions of recombinant protein. Current clinical trials of intrathecal IDUA administration are designed to inject the enzyme only once every three months, so the effectiveness of this dosing regimen remains uncertain.

SUMMARY OF THE INVENTION

Extraordinarily high levels of IDUA were expressed up to 10 months after intracerebrovectricular infusion of a IDUA expressing recombinant adeno-associated virus (rAAV) vector at birth. The present invention is directed to the intranasal administration of lysosomal storage enzymes, which provides for a less invasive delivery method and so fewer inpatient or outpatient visits. The method is employed in order to prevent, inhibit or treat neurological deterioration, such as progressive mental retardation, in mammals with a MPS disease. Lysosomal storage diseases include, but are not limited to, mucopolysaccharidosis (MPS) diseases, for instance, mucopolysaccharidosis type I, e.g., Hurler syndrome and the variants Scheie syndrome and Hurler-Scheie syndrome (a deficiency in alpha-L-iduronidase); Hunter syndrome (a deficiency of iduronate-2-sulfatase); mucopolysaccharidosis type III, e.g., Sanfilippo syndrome (A, B, C or D; a deficiency of heparan sulfate sulfatase, N-acetyl-alpha-D-glucosaminidase, acetyl CoA:alpha-glucosaminide N-acetyl transferase or N-acetylglucosamine-6-sulfate sulfatase); mucopolysaccharidosis type IV e.g., mucopolysaccharidosis type IV, e.g., Morquio syndrome (a deficiency of galactosamine-6-sulfate sulfatase or beta-galactosidase); mucopolysaccharidosis type VI, e.g., Maroteaux-Lamy syndrome (a deficiency of arylsulfatase B); mucopolysaccharidosis type II; mucopolysaccharidosis type III (A, B, C or D; a deficiency of heparan sulfate sulfatase, N-acetyl-alpha-D-glucosaminidase, acetyl CoA: alpha-glucosaminide N-acetyl transferase or N-acetylglucosamine-6-sulfate sulfatase); mucopolysaccharidosis type IV (A or B; a deficiency of galactosamine-6-sulfatase and beta-galatacosidase); mucopolysaccharidosis type VI (a deficiency of arylsulfatase B); mucopolysaccharidosis type VII (a deficiency in beta-glucuronidase); mucopolysaccharidosis type VIII (a deficiency of glucosamine-6-sulfate sulfatase); mucopolysaccharidosis type IX (a deficiency of hyaluronidase); Tay-Sachs disease (a deficiency in alpha subunit of beta-hexosaminidase); Sandhoff disease (a deficiency in both alpha and beta subunit of beta-hexosaminidase); GM1 gangliosidosis (type I or type II); Fabry disease (a deficiency in alpha galactosidase); metachromatic leukodystrophy (a deficiency of aryl sulfatase A); Pompe disease (a deficiency of acid maltase); fucosidosis (a deficiency of fucosidase); alpha-mannosidosis (a deficiency of alpha-mannosidase); beta-mannosidosis (a deficiency of beta-mannosidase); ceroid lipofuscinosis, and Gaucher disease (types I, II and III; a deficiency in glucocerebrosidase), as well as disorders such as Hermansky-Pudlak syndrome; Amaurotic idiocy; Tangier disease; aspartylglucosaminuria; congenital disorder of glycosylation, type Ia; Chediak-Higashi syndrome; macular dystrophy, corneal, 1; cystinosis, nephropathic; Fanconi-Bickel syndrome; Farber lipogranulomatosis; fibromatosis; geleophysic dysplasia; glycogen storage disease I; glycogen storage disease Ib; glycogen storage disease Ic; glycogen storage disease III; glycogen storage disease IV; glycogen storage disease V; glycogen storage disease VI; glycogen storage disease VII; glycogen storage disease 0; immunoosseous dysplasia, Schimke type; lipidosis; lipase b; mucolipidosis II; mucolipidosis II, including the variant form; mucolipidosis IV; neuraminidase deficiency with beta-galactosidase deficiency; mucolipidosis I; Niemann-Pick disease (a deficiency of sphingomyelinase); Niemann-Pick disease without sphingomyelinase deficiency (a deficiency of a npc1 gene encoding a cholesterol metabolizing enzyme); Refsum disease; Sea-blue histiocyte disease; infantile sialic acid storage disorder; sialuria; multiple sulfatase deficiency; triglyceride storage disease with impaired long-chain fatty acid oxidation; Winchester disease; Wolman disease (a deficiency of cholesterol ester hydrolase); Deoxyribonuclease I-like 1 disorder; arylsulfatase E disorder; ATPase, H+ transporting, lysosomal, subunit 1 disorder; glycogen storage disease IIb; Ras-associated protein rab9 disorder; chondrodysplasia punctata 1, X-linked recessive disorder; glycogen storage disease VIII; lysosome-associated membrane protein 2 disorder; Menkes syndrome; congenital disorder of glycosylation, type Ic; and sialuria.

Surprisingly, IDUA (alpha-L-iduronidase, i.e., laronidase) activity was detected throughout the brain within 20 minutes of administering laronidase to the nasal cavity of MPS 1 mice (mice which have no detectable IDUA activity), which was very rapid, and demonstrates effective intranasal delivery of laronidase to the CNS. Thus, although not wishing to be bound by theory, the intranasally administered enzyme likely bypasses, rather than crosses, the blood-brain barrier by traveling directly from the nasal mucosa to the brain along the olfactory and/or trigeminal neural pathway. Those results were unexpected given the large size of IDUA (that it would pass through the BBB) and that the enzyme was still active in the brain as the nasal passages have hydrolytic enzymes, e.g., proteolytic enzymes, and the pH optima of lysosomal enzymes corresponds to the pH in lysosomes. Further, it was unexpected that the enzyme reached the brain in relatively large amounts. Replacement of less than 20%, e.g., less than 10% or about 1% to 5% levels of lysosomal storage enzyme found in nondiseased mammals, may prevent or inhibit neurological degeneration in mammals with a MPS disease. Also, intranasal administration of AAV8-MCI to Idua$^{-/-}$ mice resulted in detectable IDUA activity in the olfactory bulb (about 5-fold higher than wild-type levels). In addition to providing a noninvasive method of delivery, intranasal administration, e.g., to the upper about one third of the nasal cavity, in comparison to intrathecal ERT, has the potential to easily administer an unlimited number of consecutive doses. In one embodiment, delivery is not facilitated or accomplished using iontophoresis.

In one embodiment, viral vectors, such as adenovirus, semliki forest virus and herpes simplex virus vectors, which have been shown to reach and transduce cells in the CNS following intranasal administration in rodents, as well as AAV vectors, are employed to transfer one or more genes encoding lysosomal storage enzyme to a mammal having or at risk of having a MPS disease. In one embodiment, the viral vector is an AAV vector.

Thus, the invention provides a method to prevent, inhibit or treat one or more neurological symptoms of a lysosomal storage disease in a mammal in need thereof. The method includes intranasally administering to the mammal a composition comprising an effective amount of a lysosomal storage enzyme. In one embodiment, the enzyme is alpha-L-iduronidase, iduronate-2-sulfatase, heparan sulfate sulfatase, N-acetyl-alpha-D-glucosaminidase, beta-hexosamine, alpha-galactosidase, betagalactosidase, beta-glucuronidase or glucocerebrosidase. In one embodiment, the mammal is a human. In one embodiment, multiple doses are administered, e.g., once a day, week or month. In one embodiment, the pH of the composition is about 4 to about 9, e.g., about 5 to about 7. In one embodiment, about 50 µL to about 500 µL, e.g., 200 µL to about 400 µL, is administered to the mammal. In one embodiment, the concentration of the enzyme in the composition is about 1 mg/mL to about 100 mg/mL, e.g., 5 mg/mL to about 25 mg/mL. In one embodiment, about 1 mg to about 7 mg of the enzyme is administered. The beneficial effect of the administration may be assessed by, for example, magnetic resonance imaging, functionally assessed by neuropsychological testing, and/or biochemically assessed by assaying cerebrospinal fluid for enzyme and glycosaminoglycan storage materials.

In one embodiment, a preparation of lysosomal storage enzymes, e.g., one formulated for intranasal administration, is employed. Those active agents likely reach the brain via the nasal cavity by a combination of pathways involving the olfactory nerves, vasculature, CSF, and lymphatic systems. Extracellular rather than intracellular transport is likely, due to the high concentrations of agents that reach the CNS soon after delivery. In one embodiment, the invention provides a pharmaceutical composition formulated for intranasal delivery comprising a lysosomal storage enzyme, e.g., IDUA. In one embodiment, the composition comprises drops. In one embodiment, the composition comprises a gel formulation. In one embodiment, the composition comprises an aerosol formulation. In one embodiment, the composition does not include a permeation enhancer, such as sodium glycocholate, which is a harsh detergent and bile salt that can damage and/or irritate the nasal mucosa which in turn permits entry, e.g., direct entry, to the blood stream and thereby is diluted. In contrast, the intranasal administration described herein targets the enzyme to the central nervous system along with the olfactory and trigeminal neural pathways thus lessening any dilution. Also provided is a device suitable for intranasal delivery, e.g., one comprising a lysosomal storage enzyme.

In one embodiment, for enzymes that are hydrophobic or poorly water soluble, the preparation that is employed for delivery is a lipid based microemulsion or lipid based nanoparticles, e.g., a lipid formulation such as is disclosed EP1915986 and WO2008/049588, the disclosures of which are incorporated by reference herein.

In one embodiment, the invention provides a nasal spray device for intranasal delivery of a lysosomal storage enzyme. For example, the OptiNose liquid delivery nasal spray device and other similar devices that deliver drug to both the olfactory and respiratory epithelium of the nasal cavity, while preventing delivery to the lungs by spraying only when the connection between the nose and lungs is closed, may be employed to deliver a lysosomal storage enzyme. In one embodiment, the nasal spray device is a pressurized olfactory delivery device such as the Impel NeuroPharma device, a metered dose nasal spray device or a unit dose nasal spray device. In one embodiment, the device provides for delivery of the lysosomal storage enzyme high in the nasal cavity so as to reach the olfactory epithelium in addition to the respiratory epithelium, thereby maximizing delivery to the brain.

Further provided is a composition comprising a recombinant AAV vector comprising an open reading frame for a lysosomal storage enzyme and a method to prevent, inhibit or treat one or more symptoms of a lysosomal storage disease in a mammal in need thereof, comprising: intranasally administering to the mammal a composition comprising an effective amount of a recombinant AAV comprising an open reading frame for a lysosomal storage enzyme.

BRIEF DESCRIPTION OF THE FIGURES

FIG. 3. Immunofluorescence staining with an anti-IDUA antibody reveals widespread IDUA expression, mainly in neuronal cells within areas of the limbic system. Coronal brain slices taken at the displayed coordinates from the bregma (A) were stained with an anti-human IDUA antibody. Low magnification images reveal widespread distribution of IDUA expression (red) (B, H, M). Higher-power magnification of specific regions within the section reveals IDUA expression (IDUA (red) and DAPI (blue)) in multiple areas of the limbic system including the cingulate cortex (D), septal nucleus (F), indusium griseum (G), hippocampus (CA1 (I), CA2 (J), CA3 (L), and dentate gyrus (M)), entorhinal cortex (K), and basal ganglia (caudate putamen (E)). Additionally, regions of the brain important for motor function displayed robust IDUA expression, including the primary motor cortex (C) and Purkinje cells lining the 4th ventricle in the cerebellum (O). Representative scale bars in panels (C), (I), and (O) are 100 ÿm in length.

FIG. 5. ICV infusion of AAV8-MCI into neonates normalized pathogenic storage material to levels of unaffected animals. (A) Total GAG levels in the striatum, olfactory bulb, cerebellum, hippocampus, cortex, striatum, brainstem and thalamus, and livers of wild-type, IDUA heterozygous, MPS 1, and AAV8-MCI treated MPS I mice. Data points represent brain samples microdissected from the left (red) and right (blue) hemispheres, respectively. Values are compared to respective values in untreated MPS I animals (horizontal bar: mean; ***P<0.001). (B) Punctate GM3 ganglioside accumulation is visualized in grey matter throughout the brains of MPS I animals, including the dentate gyrus and septal nucleus. This pattern of staining is absent in the brains of wild-type animals and MPS I animals treated with AAV8-MCI. Scale bars are 100 ÿm in length.

DETAILED DESCRIPTION OF THE INVENTION

Definitions

As used herein, "individual" (as in the subject of the treatment) means a mammal. Mammals include, for example, humans; non-human primates, e.g., apes and monkeys; and non-primates, e.g., dogs, cats, rats, mice, cattle, horses, sheep, and goats. Non-mammals include, for example, fish and birds.

The term "disease" or "disorder" are used interchangeably, and are used to refer to diseases or conditions wherein lack of or reduced amounts of a lysosomal storage enzyme plays a role in the disease such that a therapeutically beneficial effect can be achieved by supplementing, e.g., to at least 1% of normal levels.

"Substantially" as the term is used herein means completely or almost completely; for example, a composition that is "substantially free" of a component either has none of the component or contains such a trace amount that any relevant functional property of the composition is unaffected by the presence of the trace amount, or a compound is "substantially pure" is there are only negligible traces of impurities present.

"Treating" or "treatment" within the meaning herein refers to an alleviation of symptoms associated with a disorder or disease, "inhibiting" means inhibition of further progression or worsening of the symptoms associated with the disorder or disease, and "preventing" refers to prevention of the symptoms associated with the disorder or disease.

As used herein, an "effective amount" or a "therapeutically effective amount" of an agent of the invention e.g., a lysosomal storage enzyme or recombinant AAV encoding a lysosomal storage enzyme, refers to an amount of the agent that alleviates, in whole or in part, symptoms associated with the disorder or condition, or halts or slows further progression or worsening of those symptoms, or prevents or provides prophylaxis for the disorder or condition, e.g., an amount that is effective to prevent, inhibit or treat in the individual one or more neurological symptoms.

In particular, a "therapeutically effective amount" refers to an amount effective, at dosages and for periods of time necessary, to achieve the desired therapeutic result. A therapeutically effective amount is also one in which any toxic or detrimental effects of compounds of the invention are outweighed by the therapeutically beneficial effects.

A "vector" as used herein refers to a macromolecule or association of macromolecules that comprises or associates with a polynucleotide and which can be used to mediate delivery of the polynucleotide to a cell, either in vitro or in vivo. Illustrative vectors include, for example, plasmids, viral vectors, liposomes and other gene delivery vehicles. The polynucleotide to be delivered, sometimes referred to as a "target polynucleotide" or "transgene," may comprise a coding sequence of interest in gene therapy (such as a gene encoding a protein of therapeutic interest) and/or a selectable or detectable marker.

"AAV" is adeno-associated virus, and may be used to refer to the virus itself or derivatives thereof. The term covers all subtypes, serotypes and pseudotypes, and both naturally occurring and recombinant forms, except where required otherwise. As used herein, the term "serotype" refers to an AAV which is identified by and distinguished from other AAVs based on its binding properties, e.g., there are eleven serotypes of AAVs, AAV-1-AAV-11, and the term encompasses pseudotypes with the same binding properties. Thus, for example, AAV-5 serotypes include AAV with the binding properties of AAV-5, e.g., a pseudotyped AAV comprising AAV-5 capsid and a rAAV genome which is not derived or obtained from AAV-5 or which genome is chimeric. The abbreviation "rAAV" refers to recombinant adeno-associated virus, also referred to as a recombinant AAV vector (or "rAAV vector").

An "AAV virus" refers to a viral particle composed of at least one AAV capsid protein and an encapsidated polynucleotide. If the particle comprises a heterologous polynucleotide (i.e., a polynucleotide other than a wild-type AAV genome such as a transgene to be delivered to a mammalian cell), it is typically referred to as "rAAV". An AAV "capsid protein" includes a capsid protein of a wild-type AAV, as well as modified forms of an AAV capsid protein which are structurally and or functionally capable of packaging a rAAV genome and bind to at least one specific cellular receptor which may be different than a receptor employed by wild type AAV. A modified AAV capsid protein includes a chimeric AAV capsid protein such as one having amino acid sequences from two or more serotypes of AAV, e.g., a capsid protein formed from a portion of the capsid protein from AAV-5 fused or linked to a portion of the capsid protein from AAV-2, and a AAV capsid protein having a tag or other detectable non-AAV capsid peptide or protein fused or linked to the AAV capsid protein, e.g., a portion of an antibody molecule which binds the transferrin receptor may be recombinantly fused to the AAV-2 capsid protein.

A "pseudotyped" rAAV is an infectious virus having any combination of an AAV capsid protein and an AAV genome. Capsid proteins from any AAV serotype may be employed with a rAAV genome which is derived or obtainable from a wild-type AAV genome of a different serotype or which is a chimeric genome, i.e., formed from AAV DNA from two or more different serotypes, e.g., a chimeric genome having 2 inverted terminal repeats (ITRs), each ITR from a different serotype or chimeric ITRs. The use of chimeric genomes such as those comprising ITRs from two AAV serotypes or chimeric ITRs can result in directional recombination which may further enhance the production of transcriptionally active intermolecular concatamers. Thus, the 5N and 3N ITRs within a rAAV vector of the invention may be homologous, i.e., from the same serotype, heterologous, i.e., from different serotypes, or chimeric, i.e., an ITR which has ITR sequences from more than one AAV serotype.

Pathways for Delivery

Despite the immense network of the cerebral vasculature, systemic delivery of therapeutics to the central nervous system (CNS) is not effective for greater than 98% of small molecules and for nearly 100% of large molecules (Partridge, 2005). The lack of effectiveness is due to the presence of the blood-brain barrier (BBB), which prevents most foreign substances, even many beneficial therapeutics, from entering the brain from the circulating blood. While certain small molecule, peptide, and protein therapeutics given systemically reach the brain parenchyma by crossing the BBB (Banks, 2008), generally high systemic doses are needed to achieve therapeutic levels, which can lead to adverse effects in the body. Therapeutics can be introduced directly into the CNS by intracerebroventricular or intraparenchymal injections; however, for multiple dosing regimens both delivery methods are invasive, risky, and expensive techniques requiring surgical expertise. Additional limitations to the utility of these methods are inadequate CNS exposure due to slow diffusion from the injection site and rapid turnover of the cerebrospinal fluid (CSF). Intranasal delivery has come to the forefront as an alternative to invasive delivery methods to bypass the BBB and rapidly target therapeutics directly to the CNS utilizing pathways along olfactory and trigeminal nerves innervating the nasal passages (Frey II, 2002; Thorne et al., 2004; Dhanda et al., 2005).

While the exact mechanisms underlying intranasal drug delivery to the CNS are not entirely understood, an accumulating body of evidence demonstrates that pathways involving nerves connecting the nasal passages to the brain and spinal cord are important. In addition, pathways involving the vasculature, cerebrospinal fluid, and lymphatic system have been implicated in the transport of molecules from the nasal cavity to the CNS. It is likely that a combination of these pathways is responsible, although one pathway may predominate, depending on the properties of the therapeutic, the characteristics of the formulation, and the delivery device used.

Therapeutics can rapidly gain access to the CNS following intranasal administration along olfactory nerve pathways leading from the nasal cavity directly to the CNS. Olfactory nerve pathways are a major component of intranasal delivery, evidenced by the fact that fluorescent tracers are associated with olfactory nerves as they traverse the cribriform plate (Jansson et al., 2002), drug concentrations in the olfactory bulbs are generally among the highest CNS concentrations observed (Thorne et al., 2004; Banks et al., 2004; Graff et al., 2005a); Nonaka et al., 2008; Ross et al., 2004; Ross et al., 2008; Thorne et al., 2008), and a strong, positive correlation exists between concentrations in the olfactory epithelium and olfactory bulbs (Dhuria et al., 2009a).

Olfactory pathways arise in the upper portion of the nasal passages, in the olfactory region, where olfactory receptor neurons (ORNs) are interspersed among supporting cells (sustentacular cells), microvillar cells, and basal cells. ORNs mediate the sense of smell by conveying sensory information from the peripheral environment to the CNS (Clerico et al., 2003). Beneath the epithelium, the lamina propria contains mucus secreting Bowman's glands, axons, blood vessels, lymphatic vessels, and connective tissue. The dendrites of ORNs extend into the mucous layer of the olfactory epithelium, while axons of these bipolar neurons extend centrally through the lamina propria and through perforations in the cribriform plate of the ethmoid bone, which separates the nasal and cranial cavities. The axons of ORNs pass through the subarachnoid space containing CSF and terminate on mitral cells in the olfactory bulbs. From there, neural projections extend to multiple brain regions including the olfactory tract, anterior olfactory nucleus, piriform cortex, amygdala, and hypothalamus (Buck, 2000). In addition to ORNs, chemosensory neurons located at the anterior tip of the nasal cavity in the Grueneberg ganglion lead into the olfactory bulbs (Fuss et al., 2005; Koos et al., 2005).

The unique characteristics of the ORNs contribute to a dynamic cellular environment critical for intranasal delivery to the CNS. Due to the direct contact with toxins in the external environment, ORNs regenerate every 3-4 weeks from basal cells residing in the olfactory epithelium (Mackay-Sim, 2003). Special Schwann cell-like cells called olfactory ensheathing cells (OECs) envelope the axons of ORNs and have an important role in axonal regeneration, regrowth, and remyelination (Field et al., 2003; Li et al., 2005a; Li et al., 2005b). The OECs create continuous, fluid-filled perineurial channels that, interestingly, remain open, despite the degeneration and regeneration of ORNs (Williams et al., 2004).

Given the unique environment of the olfactory epithelium, it is possible for intranasally administered therapeutics to reach the CNS via extracellular or intracellular mechanisms of transport along olfactory nerves. Extracellular transport mechanisms involve the rapid movement of molecules between cells in the nasal epithelium, requiring only several minutes to 30 minutes for a drug to reach the olfactory bulbs and other areas of the CNS after intranasal administration (Frey II, 2002; Balin et al., 1986). Transport likely involves bulk flow mechanisms (Thorne et al., 2004; Thorne et al., 2001) within the channels created by the OECs. Drugs may also be propelled within these channels by the structural changes that occur during depolarization and axonal propagation of the action potential in adjacent axons (Luzzati et al., 2004). Intracellular transport mechanisms involve the uptake of molecules into ORNs by passive diffusion, receptor-mediated endocytosis or adsorptive endocytosis, followed by slower axonal transport, taking several hours to days for a drug to appear in the olfactory bulbs and other brain areas (Baker et al., 1986; Broadwell et al., 1985; Kristensson et al., 1971). Intracellular transport in ORNs has been demonstrated for small, lipophilic molecules such as gold particles (de Lorenzo, 1970; Gopinath et al., 1978), aluminum salts (Perl et al., 1987), and for substances with receptors on ORNs such as WGA-HRP (Thorne et al., 1995; Baker et al., 1986; Itaya et al., 1986; Shipley, 1985). Intracellular mechanisms, while important for certain therapeutics, are not likely to be the predominant mode of transport into the CNS. While some large molecules, such as galanin-like peptide (GALP), exhibit saturable transport pathways into the CNS (Nonaka et al., 2008), for other large molecules such as NGF and insulin-like growth factor-I (IGF-I), intranasal delivery into the brain is nonsaturable and not receptor mediated (Thorne et al., 2004; Chen et al., 1998; Zhao et al., 2004), An often overlooked but important pathway connecting the nasal passages to the CNS involves the trigeminal nerve, which innervates the respiratory and olfactory epithelium of the nasal passages and enters the CNS in the pons (Clerico et al., 2003; Graff et al., 2003). Interestingly, a small portion of the trigeminal nerve also terminates in the olfactory bulbs (Schaefer et al., 2002). The cellular composition of the respiratory region of the nasal passages is different from that of the olfactory region, with ciliated epithelial cells distributed among mucus secreting goblet cells. These cells contribute to mucociliary clearance mechanisms that remove mucus along with foreign substances from the nasal cavity to the nasopharynx. The trigeminal nerve conveys sensory information from the nasal cavity, the oral cavity, the eyelids, and the cornea, to the CNS via the ophthalmic division (V1), the maxillary division (V2), or the mandibular division (V3) of the trigeminal nerve (Clerico et al., 2003; Gray, 1978). Branches from the ophthalmic division of the trigeminal nerve provide innervation to the dorsal nasal mucosa and the anterior portion of the nose, while branches of the maxillary division provide innervation to the lateral walls of the nasal mucosa. The mandibular division of the trigeminal nerve extends to the lower jaw and teeth, with no direct neural inputs to the nasal cavity. The three branches of the trigeminal nerve come together at the trigeminal ganglion and extend centrally to enter the brain at the level of the pons, terminating in the spinal trigeminal nuclei in the brainstem. A unique feature of the trigeminal nerve is that it enters the brain from the respiratory epithelium of the nasal passages at two sites: (1) through the anterior lacerated foramen near the pons and (2) through the cribriform plate near the olfactory bulbs, creating entry points into both caudal and rostral brain areas following intranasal administration. It is also likely that other nerves that innervate the face and head, such as the facial nerve, or other sensory structures in the nasal cavity, such as the Grueneberg ganglion, may provide entry points for intranasally applied therapeutics into the CNS.

Traditionally, the intranasal route of administration has been utilized to deliver drugs to the systemic circulation via absorption into the capillary blood vessels underlying the nasal mucosa. The nasal mucosa is highly vascular, receiving its blood supply from branches of the maxillary, ophthalmic and facial arteries, which arise from the carotid artery (Clerico et al., 2003; Cauna, 1982). The olfactory mucosa receives blood from small branches of the ophthalmic artery, whereas the respiratory mucosa receives blood from a large caliber arterial branch of the maxillary artery (DeSesso, 1993). The relative density of blood vessels is greater in the respiratory mucosa compared to the olfactory mucosa, making the former region an ideal site for absorption into the blood (DeSesso, 1993). The vasculature in the respiratory region contains a mix of continuous and fenestrated endothelia (Grevers et al., 1987; Van Diest et al., 1979), allowing both small and large molecules to enter the systemic circulation following nasal administration.

Delivery to the CNS following absorption into the systemic circulation and subsequent transport across the BBB is possible, especially for small, lipophilic drugs, which more easily enter the blood stream and cross the BBB compared to large, hydrophilic therapeutics such as peptides and proteins.

Increasing evidence is emerging suggesting that mechanisms involving channels associated with blood vessels, or perivascular channels, are involved in intranasal drug delivery to the CNS. Perivascular spaces are bound by the outermost layer of blood vessels and the basement membrane of the surrounding tissue (Pollock et al., 1997). These perivascular spaces act as a lymphatic system for the brain, where neuron-derived substances are cleared from brain interstitial fluid by entering perivascular channels associated with cerebral blood vessels. Perivascular transport is due to bulk flow mechanisms, as opposed to diffusion alone (Cserr et al., 1981; Groothuis et al., 2007), and arterial pulsations are also a driving force for perivascular transport (Rennels et al., 1985; Rennels et al., 1985). Intranasally applied drugs can move into perivascular spaces in the nasal passages or after reaching the brain and the widespread distribution observed within the CNS could be due to perivascular transport mechanisms (Thorne et al., 2004).

Pathways connecting the subarachnoid space containing CSF, perineurial spaces encompassing olfactory nerves, and the nasal lymphatics are important for CSF drainage and these same pathways provide access for intranasally applied therapeutics to the CSF and other areas of the CNS. Several studies document that tracers injected into the CSF in the cerebral ventricles or subarachnoid space drain to the underside of the olfactory bulbs into channels associated with olfactory nerves traversing the cribriform plate and reach the nasal lymphatic system and cervical lymph nodes (Bradbury et al., 1983; Hatterer et al., 2006; Johnston et al., 2004a); Kida et al., 1993; Walter et al., 2006a; Walter et al., 2006b). Drugs can access the CNS via these same pathways after intranasal administration, moving from the nasal passages to the CSF to the brain interstitial spaces and perivascular spaces for distribution throughout the brain. These drainage pathways are significant in a number of animal species (sheep, rabbits, and rats) accounting for approximately 50% of CSF clearance (Bradbury et al., 1981; Boulton et al., 1999; Boulton et al., 1996; Cserr et al., 1992). Pathways between the nasal passages and the CSF are still important and functional in humans, evidenced by the fact that therapeutics are directly delivered to the CSF following intranasal delivery, without entering the blood to an appreciable extent (Born et al., 2002). A number of intranasal studies demonstrate that drugs gain direct access to the CSF from the nasal cavity, followed by subsequent distribution to the brain and spinal cord. Many intranasally applied molecules rapidly enter the CSF, and this transport is dependent on the lipophilicity, molecular weight, and degree of ionization of the molecules (Dhanda et al., 2005; Born et al., 2002; Kumar et al., 1974; Sakane et al., 1995; Sakane et al., 1994; Wang et al., 2007). Assessing distribution into the CSF can provide information on the mechanism of intranasal delivery.

Intranasal Delivery of Enzymes to the CNS

The present invention provides for noninvasive intranasal administration which rapidly targets large enzymes to the CNS. Such enzymes, when delivered intranasally, likely travel within minutes along the olfactory and trigeminal neural pathways from the nasal mucosa to the brain and enter the perivascular spaces of blood vessels of the cerebrovasculature through which they are rapidly dispersed throughout the CNS.

As reported in therecent review by Dhuria et al. (2010), the largest therapeutic protein reported to be delivered to the brain after intranasal administration in animals is nerve growth factor (NGF, 27.5 kDa), which reached multiple brain regions in rats, with the greatest concentrations in the olfactory bulbs. See Chen et al., (1998) and Frey et al., (1997). Most LSDs are missing enzymes which are much larger and more complex than the smaller peptides and neurotrophic factors previously found to enter the brain following intranasal administration. For example, glycosylated human recombinant IDUA, currently used for the treatment of Hurler-Scheie forms of MPS I, has a molecular weight of approximately 83 kDa (Aldurazyme package insert—manufactured by Biomarin Pharmaceuticals Inc. and marketed by Genzyme Corporation). U.S. Pat. No. 6,509,611 discloses that the specific activity of the α-L-iduronidase is in excess of 200,000 units per milligram protein. Such as in excess of about 240,000 units per milligram protein, and that molecular weight of the α-L-iduronidase is about 82,000 daltons, about 70,000 daltons being amino acid, and about 12,000 daltons being carbohydrates.

In other LSDs, even larger and more complex enzymes are deficient in the brain. For example, in GM2 Gangliosidosis, β-Hexosaminidase is missing or altered (see, R. J. A. Wanders in Inherited Metabolic Diseases: A Clinical Approach edited by Georg Hoffman et al.). Hexosaminidase B1 has a molecular weight of about 93,000 daltons while Hexosaminidase A1 has a molecular weight of about 170,000. Thus, the size of enzymes missing in LSDs affecting the CNS is much larger than that of most neurotrophic factors such as NGF (26.5 kDa) which were previously intranasally delivered to the brain (Chen et al. (1998) and Frey et al. (1997)). In addition, enzymes have a critical active site, which must remain intact throughout the delivery process if the enzyme is to carry out catalysis of the required reaction. Further, neurotrophic factors are active at concentrations far lower than those required for enzyme catalysis. NGF, for example, has been shown to produce its effects on the brain at concentrations as low as 5.8 picomolar ($5.8 \times 10^{-12}$ M). S. Buxer et al. has reported that human recombinant human NGF stimulates a significant increase in the dopamine content of PC12 cells with an ED50 of 5.8+/−2.7 pM (Buxer et al., (1991). Certain other neurotrophins such as activity dependent neurotrophic factor (ADNF) are neuroprotective at concentrations even 1000 times lower than those required for NGF activity (i.e., in the femtomolar range ($10^{-15}$ M) (Gozes et al., (2000)).

Prior to the present disclosure it was unknown whether intranasal administration of IDUA and other enzymes missing in LSDs would result in catalytic and therapeutic concentrations of these enzymes reaching the brain, since the brain concentrations required are many orders of magnitude greater than those required for neurotrophins and since these enzymes are so much larger. In addition, the larger size of these enzymes also means that formulating them for intranasal delivery is more difficult since higher concentrations are needed in order to obtain the same molar concentration and molar dose in the small volumes suitable for intranasal delivery.

Compositions and Formulations of the Invention

Protective barriers in the nasal mucosa contribute to the low efficiency of delivery observed following intranasal administration, with typically less than 1% of the administered dose reaching the brain (Illum, 2004; Thorne et al., 2001). Nasal mucociliary clearance mechanisms are in place to remove foreign substances towards the nasopharynx, which is accomplished by dissolution of substances in the mucus layer and transport by ciliated cells in the nasal epithelium. Efflux transport proteins, such as p-glycoprotein (P-gp) and multidrug resistance-associated protein (MRP1), are expressed in the nasal mucosa (Kandimalla et al., 2005a; Graff et al., 2005b; Wioland et al., 2000), and can significantly limit the uptake of substrates into the brain (Graff et al., 2003; Graff et al., 2005b; Kandimalla et al., 2005b). In addition, there is evidence of drug metabolizing enzymes (Minn et al., 2002; Sarkar, 1992) and tight junction proteins (Miragall et al., 1994) in the nasal epithelium, which can limit the efficiency of intranasal delivery to the CNS. The nasal vasculature can also be a limiting factor as it clears inhaled toxins and intranasally applied therapeutics into the systemic circulation for detoxification and elimination. Common themes in formulation approaches to overcome these barriers involve improving drug solubility, increasing permeability across the nasal epithelium, reducing clearance from the nasal passages, or a combination approach.

In order for a therapeutic to have adequate absorption and bioavailability in the CNS after intranasal administration, it should have sufficient solubility at the site of delivery in the nasal epithelium. Drugs may be encapsulated in carriers, such as cyclodextrins either alpha or beta, microemulsions, and nanoparticles, to overcome these issues for intranasal delivery to the CNS.

Compositions of the invention having an enzyme or viral vector described herein, may be employed, alone or in combination with another medicament. The compositions can appear in conventional forms, for example, aerosols, solutions, suspensions, or topical applications, or in lyophilized form.

Typical compositions include an agent of the invention and a pharmaceutically acceptable excipient which can be a carrier or a diluent. For example, the active agent may be mixed with a carrier, or diluted by a carrier, or enclosed within a carrier. When the active agent is mixed with a carrier, or when the carrier serves as a diluent, it can be solid, semi-solid, or liquid material that acts as a vehicle, excipient, or medium for the active agent. Some examples of suitable carriers are water, salt solutions, alcohols, polyethylene glycols, polyhydroxyethoxylated castor oil, peanut oil, olive oil, gelatin, lactose, terra alba, sucrose, dextrin, magnesium carbonate, sugar, cyclodextrin, amylose, magnesium stearate, talc, gelatin, agar, pectin, acacia, stearic acid or lower alkyl ethers of cellulose, silicic acid, fatty acids, fatty acid amines, fatty acid monoglycerides and diglycerides, pentaerythritol fatty acid esters, polyoxyethylene, hydroxymethylcellulose and polyvinylpyrrolidone. Similarly, the carrier or diluent can include any sustained release material known in the art, such as glyceryl monostearate or glyceryl distearate, alone or mixed with a wax.

The formulations can be mixed with auxiliary agents which do not deleteriously react with the active agent. Such additives can include wetting agents, emulsifying and suspending agents, salt for influencing osmotic pressure, buffers and/or coloring substances preserving agents, sweetening agents or flavoring agents. The compositions can also be sterilized if desired.

If a liquid carrier is used, the preparation can be in the form of a liquid such as an aqueous liquid suspension or solution. Acceptable solvents or vehicles include sterilized water, Ringer's solution, or an isotonic aqueous saline solution.

The agent may be provided as a powder suitable for reconstitution with an appropriate solution as described above. Examples of these include, but are not limited to, freeze dried, rotary dried or spray dried powders, amorphous powders, granules, precipitates, or particulates. The composition can optionally contain stabilizers, pH modifiers, surfactants, bioavailability modifiers and combinations of these. A unit dosage form can be in individual containers or in multi-dose containers.

Compositions contemplated by the present invention may include, for example, micelles or liposomes, or some other encapsulated form, or can be administered in an extended release form to provide a prolonged storage and/or delivery effect, e.g., using biodegradable polymers, e.g., polylactide-polyglycolide. Examples of other biodegradable polymers include poly(orthoesters) and poly(anhydrides).

For instance, microemulsion and nanoemulsion formulations can improve drug solubility and opportunities for direct transport into the CNS. Polymeric nanoparticles, e.g., comprised of a hydrophobic core of polylactic acid (PLA) and a hydrophilic shell of methoxy-poly(ethylene glycol) (MPEG), have been evaluated for improving solubility and intranasal drug targeting to the CNS. Regional differences in targeting between the microemulsion and nanoparticle formulations may be due to differences in particle size.

Liposomes are very simple structures consisting of one or more lipid bilayers of amphiphilic lipids, i.e., phospholipids or cholesterol. The lipophilic moiety of the bilayers is turned towards each other and creates an inner hydrophobic environment in the membrane. Liposomes are suitable drug carriers for some lipophilic drugs which can be associated with the non-polar parts of lipid bilayers if they fit in size and geometry. The size of liposomes varies from 20 nm to few μm.

Mixed micelles are efficient detergent structures which are composed of bile salts, phospholipids, tri, di- and monoglycerides, fatty acids, free cholesterol and fat soluble micronutrients. As long-chain phospholipids are known to form bilayers when dispersed in water, the preferred phase of short chain analogues is the spherical micellar phase. A micellar solution is a thermodynamically stable system formed spontaneously in water and organic solvents. The interaction between micelles and hydrophobic/lipophilic drugs leads to the formation of mixed micelles (MM), often called swallen micelles, too. In the human body, they incorporate hydrophobic compounds with low aqueous solubility and act as a reservoir for products of digestion, e.g. monoglycerides.

Lipid microparticles includes lipid nano- and microspheres. Microspheres are generally defined as small spherical particles made of any material which are sized from about 0.2 to 100 μm. Smaller spheres below 200 nm are usually called nanospheres. Lipid microspheres are homogeneous oil/water microemulsions similar to commercially available fat emulsions, and are prepared by an intensive sonication procedure or high pressure emulsifying methods (grinding methods). The natural surfactant lecithin lowers the surface tension of the liquid, thus acting as an emulsifier to form a stable emulsion. The structure and composition of lipid nanospheres is similar to those of lipid microspheres, but with a smaller diameter.

Polymeric nanoparticles serve as carriers for a broad variety of ingredients. The active components may be either dissolved in the polymetric matrix or entrapped or adsorbed onto the particle surface. Polymers suitable for the preparation of organic nanoparticles include cellulose derivatives and polyesters such as poly(lactic acid), poly(glycolic acid) and their copolymer. Due to their small size, their large surface area/volume ratio and the possibility of functionalization of the interface, polymeric nanoparticles are ideal carrier and release systems. If the particle size is below 50 nm, they are no longer recognized as particles by many biological and also synthetic barrier layers, but act similar to molecularly disperse systems.

Thus, the composition of the invention can be formulated to provide quick, sustained, controlled, or delayed release, or any combination thereof, of the active agent after administration to the individual by employing procedures well known in the art. In one embodiment, the enzyme is in an isotonic or hypotonic solution. In one embodiment, for enzymes that are not water soluble, a lipid based delivery vehicle may be employed, e.g., a microemulsion such as that described in WO 2008/049588, the disclosure of which is incorporated by reference herein, or liposomes. In one embodiment, the enzyme is about 0.1 mg/mL to about 100 mg/mL, e.g., about 5 mg/mL to about 50 mg/mL. In one embodiment, a volume of about 50 μL to about 200 μL is administered per nostril.

In one embodiment, the preparation can contain a compound of the invention, dissolved or suspended in a liquid carrier, such as an aqueous carrier, for aerosol application. The carrier can contain additives such as solubilizing agents, e.g., propylene glycol, surfactants, absorption enhancers such as lecithin (phosphatidylcholine) or cyclodextrin, or preservatives such as parabens. Fro example, in addition to solubility, efficient delivery to the CNS following intranasal administration may be dependent on membrane permeability. For enzymes where paracellular transport is hindered due to size and polarity, improving membrane permeability may enhance extracellular mechanisms of transport to the CNS along olfactory and trigeminal nerves. One approach to modifying membrane permeability within the nasal epithelium is by using permeation enhancers, such as surfactants, e.g., lauroylcarnitine (LC), bile salts, lipids, cyclodextrins, polymers, or tight junction modifiers.

Changes in osmolarity of a formulation can cause cells to expand or shrink, enhancing intracellular or extracellular transport mechanisms along olfactory and trigeminal nerves to the CNS. In addition to cell shrinking, it is possible that the hypertonic solution caused epithelial changes, such as increased mucus secretion, that hindered transport into the brain.

The pH of the nasal formulation and ionization state of the drug can affect the efficiency of intranasal delivery to the CNS. Sakane et al. (1994) showed that delivery of sulphisomidine to the CSF following intranasal administration increased as the fraction of unionized drug increased. For example, positively charged drugs may form electrostatic interactions with the negatively charged nasal epithelial cells, effectively hindering transport beyond the nasal mucosa and into the brain.

Mucociliary clearance mechanisms rapidly remove drugs from the delivery site, reducing contact with the nasal epithelium and delivery into the CNS after intranasal administration. Several approaches, including use of mucoadhesive agents, e.g., sodium hyaluronate, chitosan, acrylic acid derivatives, lectin, and low methylated pectin, surface-engineered nanoparticles, efflux transporter inhibitors, and vasoconstrictors, have been utilized to reduce clearance, to prolong the residence time of the formulation at the delivery site, and to increase transport along direct pathways to the CNS. Increasing the residence time at the delivery site potentially enhances delivery into the CNS along olfactory and trigeminal nerves, the vasculature, or CSF and lymphatic channels. Mucoadhesives used in combination with microemulsion formulations show the greatest potential in terms of enhancing brain uptake and drug targeting to the CNS.

Surface engineering of nanoparticles with ligands that bind to specific cell surfaces is a promising approach to reduce clearance and enhance targeted delivery to the CNS. For example, the lectin, ulex europeus agglutinin I (UEA I), binds to receptors located predominantly in the olfactory epithelium, while WGA recognizes sugar molecules and binds to receptors expressed throughout the olfactory and respiratory epithelia. UEA I nanoparticles could enhance delivery to the CNS along olfactory pathways, whereas WGA nanoparticles could enhance delivery to the CNS along multiple pathways, including neural and vascular pathways. Intranasal studies using UEA I or WGA conjugated PEG-PLA nanoparticles loaded with a fluorescent marker resulted in increased delivery to different brain areas, including the olfactory bulbs, olfactory tract, cerebrum, and cerebellum, compared to unmodified nanoparticles, without resulting in nasal ciliotoxicity (Gao et al., 2007a; Gao et al., 2006).

Reducing clearance from the nasal cavity due to efflux from transport proteins or due to absorption into the nasal vasculature are additional strategies that have been explored to increase the residence time at the delivery site and to enhance the efficiency of intranasal delivery to the CNS. Intranasal pretreatment with an inhibitor (rifampin) of the P-gp efflux transport protein prior to intranasal administration of a P-gp substrate (verapamil) resulted in significantly greater brain uptake as a result of reduced clearance from P-gp-mediated efflux (Graff et al., 2003). Reducing clearance into the blood from the site of delivery by using a vasoconstrictor could allow more of the drug to be available for direct transport into the CNS. Intranasal administration of hypocretin-1 with the vasoconstrictor, phenylephrine, resulted in reduced absorption of hypocretin-1 into the blood (Dhuria et al., 2009a). The reduced clearance from the nasal epithelium into the blood led to increased deposition in the olfactory epithelium and increased delivery along olfactory nerve pathways to the olfactory bulbs.

IDUA and other enzymes needed to treat LSDs may be formulated as stabilized enzyme crystals as described in U.S. Pat. No. 7,351,798, the disclosure of which is incorporated by reference herein. For example, intranasal administration of enzyme crystals would result in dissolution of the crystals in the nasal mucous layer on the nasal epithelium. In one embodiment, the dissolved enzyme is the transported to the brain along the neural pathways. The formulations in WO/2008/049588, the disclosure of which is incorporated by reference herein, related to intranasal delivery of poorly-water soluble compounds to the brain using lipid formulations may be useful for targeting IDUA and other missing enzymes in LSDs to the CNS.

Vaka et al., Pharmazie, 65: 690 (2010), have reported that using in vivo studies employing brain microdialysis in rats demonstrated that intranasal administration of NGF formulation with 0.5% peppermint oil enhanced the bioavailability by about 8-fold compared to rats administered with NGF alone. The bioavailability of NGF in the brain could be enhanced by intranasal administration of peppermint oil. This may be useful in enhancing intranasal delivery of IDUA and other missing enzymes in LSDs to the CNS.

The agent of the invention may be effective over a wide dosage range. For example, in the treatment of adult humans, dosages from about 0.05 to about 50 mg, such as from about 1 to about 20 mg, or about 2 and about 5 mg, per day, week or month may be used. In one embodiment 10 µg to about 30 mg is administered, e.g., about 0.2 mg to about 20 mg or about 1.0 mg to about 10 mg. In one embodiment, the intravenous dose administered is about 0.2 mg/kg to about 0.9 mg/kg, e.g., about 0.58 mg/kg. One dosage is about 10 mg to about 1000 mg per day, week or month. In choosing a regimen for individual it can frequently be necessary to begin with a higher dosage and when the condition is under control to reduce the dosage. The exact dosage will depend upon the activity of the agent and the form in which administered, the individual to be treated and the body weight of the individual to be treated, and the experience of the physician or veterinarian in charge.

Generally, the compounds of the invention are dispensed in unit dosage form including from about 0.05 mg to about 100 mg of active ingredient together with a pharmaceutically acceptable carrier per unit dosage.

Usually, dosage forms suitable for nasal administration include from about 125 µg to about 125 mg, e.g., from about 250 µg to about 50 mg, or from about 2.5 mg to about 25 mg, of the compounds admixed with a pharmaceutically acceptable carrier or diluent.

Dosage forms can be administered daily, or more than once a day, such as twice or thrice daily. Alternatively dosage forms can be administered less frequently than daily, such as every other day, or weekly, if found to be advisable by a prescribing physician.

Exemplary Administration Methods

Optimal delivery to the CNS along neural pathways is associated with delivery of the agent to the upper third of the nasal cavity (Hanson et al., 2008). Although a supine position may be employed another position for targeting the olfactory region is with the "praying to Mecca" position, with the head down-and-forward. A supine position with the head angle at 70° or 90° may be suitable for efficient delivery to the CSF using a tube inserted into the nostrils to deliver the drug via intranasal administration (van den Berg et al., (2002)).

For intranasal drug administration nose drops may be administered over a period of 10-20 minutes to alternating nostrils every 1-2 minutes to allow the solution to be absorbed into the nasal epithelium (Thorne et al., 2004; Capsoni et al., 2002; Ross et al., 2004; Ross et al., 2008; Dhuria et al., 2009a; Dhuria et al., 2009b; Francis et al., 2008; Martinez et al., 2008). This noninvasive method does not involve inserting the device into the nostril. Instead, drops are placed at the opening of the nostril, allowing the individual to sniff the drop into the nasal cavity. Other administration methods in anesthetized individual involve sealing the esophagus and inserting a breathing tube into the trachea to prevent the nasal formulation from being swallowed and to eliminate issues related to respiratory distress (Chow et al., 1999; Chow et al., 2001; Fliedner et al., 2006; Dahlin et al., 2001). Flexible tubing can be inserted into the nostrils for localized delivery of a small volume of the drug solution to the respiratory or olfactory epithelia, depending on the length of the tubing (Chow et al., 1999; Van den Berg et al., 2003; van den Berg et al., 2004a; Banks et al., 2004; van den Berg et al., 2002; Vyas et al., 2006a; Charlton et al., 2007a; Gao et al., 2007a).

Nasal delivery devices, such as sprays, nose droppers or needle-less syringes, may be employed to target the agent to different regions of the nasal cavity. OptiMist™ is a breath actuated device that targets liquid or powder nasal formulations to the nasal cavity, including the olfactory region, without deposition in the lungs or esophagus (Djupesland et al., 2006). The ViaNase™ device can also be used to target a nasal spray to the olfactory and respiratory epithelia of the nasal cavity. Nasal drops tend to deposit on the nasal floor and are subjected to rapid mucociliary clearance, while nasal sprays are distributed to the middle meatus of the nasal mucosa (Scheibe et al., 2008).

Delivery volume is selected so as to cover the surface area of the nasal passages in order for the agent to reach the respiratory and olfactory epithelia for transport to the CNS along trigeminal and olfactory neural pathways. For example, a total volume of 40-100 mL given as 6-10 mL nose drops using a device or given all at once using flexible tubing may be employed. The volume of the nose drop may also affect deposition in the nasal passages, where a small volume drop (e.g., 2 mL) will likely result in deposition primarily in the respiratory epithelium and a large volume drop (e.g., 20 mL) may result in deposition in the nasopharynx. If tubing is used for drug administration, lower volumes of 20-40 mL may be used for intranasal delivery because there is less surface area to cover (Van den Berg et al., 2003; van den Berg et al., 2004b; van den Berg et al., 2002; Gao et al., 2007a; Charlton et al., 2007b). Alternatively, a total volume of 24 mL may be administered in 3-4 mL nose drops. In humans, the nasal cavity has a volume of 25 cm3 and the olfactory region occupies 8% of the nasal cavity surface area (DeSesso, 1993). Intranasal drug delivery volumes of 0.4 mL administered in 100 mL aliquots clearly result in CNS effects in humans (Reger et al., 2006; Reger et al., 2008a; Reger et al., 2008b; Benedict et al., 2007; Hallschmid et al., 2008) and 200 mL administered in 100 mL aliquots may also be sufficient.

Comparing ratios of brain concentrations to blood concentrations after intranasal and intravenous administration provides an assessment of direct transport to the brain (Chow et al., 1999; Dhuria et al., 2009a; Dhuria et al., 2009b). Brain-to-blood ratios that are greater with intranasal compared to intravenous administration indicate that direct pathways other than the vasculature are important for transport from the nasal cavity to the CNS. An alternative to determining brain-to-blood concentration ratios includes designing experiments such that blood exposure after intranasal and intravenous administration are similar (i.e., similar AUC) (Thorne et al., 2004; Ross et al., 2004), which allows for direct comparisons of concentrations between different routes of administration. Drug targeting efficiency (DTE) or the drug targeting index (DTI) compares the ratio of the brain AUC/blood AUC after intranasal administration to that after intravenous administration (Dhuria et al., 2009a; Zhang et al., 2004a). Direct transport percentage (DTP),which can be derived from the DTE, determines the fraction of the brain AUC observed after intranasal administration involving pathways other than the vasculature (Dhuria et al., 2009b; Zhang et al., 2004a).

The invention will be described by the following non-limiting examples.

EXAMPLE I

Intranasal Administration of IDUA Leads to Widespread Distribution in the Brains of Mice IDUA−/− mice were anesthetized and treated with either 24 µL of PBS vehicle or laronidase (Aldurazyme) that had been concentrated by centrifugation in an Amicon Centriplus YM-10 column to a final concentration of about 1.5 mg/mL. Prior to concentration, the laronidase was diluted with two parts Elliots B solution (which is comparable in pH, electrolyte composition, glucose content, and osmolarity to cerebrospinal fluid, and includes sodium chloride, sodium bicarbonate, dextrose, magnesium sulfate, potassium chloride, calcium chloride, and sodium phosphate, resulting in sodium 149 mEq/liter, potassium 4.0 mEq/liter, calcium 2.7 mEq/liter, magnesium 2.4 mEq/liter, bicarbonate 22.6 mEq/liter, chloride 132 mEq/liter, sulfate 2.4 mEq/liter, and phosphate 1.5 mEq/liter). The treatments were administered by applying a series of eight 3 µL drops to the nasal cavity of each mouse at one-minute intervals using a micropipet, resulting in a total dose of 36 µg of laronidase per treated mouse. Since Aldurazyme (laronidase) has a specific activity of 172 U/mg, this corresponds to a dose of 6.2 units, where one unit is the amount of enzyme that converts one µmole of substrate per minute. Twenty minutes following the administration of the first drop, the animals were perfused with PBS (saline) solution, and the brains were harvested and microdissected into the indicated regions. The brain samples were then homogenized in 250 µL of PBS, and IDUA activity was determined using a fluorimetric enzyme assay.

Figure 1:
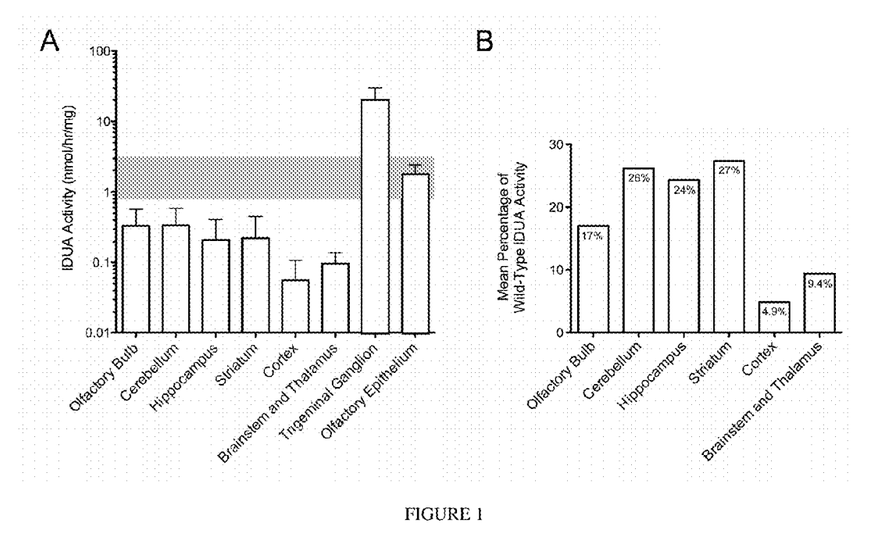
FIG. 1. Widespread IDUA activity is detected in the brains of Idua−/− mice 20 minutes after intranasal administration of laronidase. (A) IDUA activity is detected in all regions of the brain assayed as well as within the trigeminal ganglion and olfactory epithelium. Values plotted have been normalized to the background activity detected by the assay, defined as the amount of activity detected in tissue from Idua−/− animals. The grey bar represents wild-type activity levels. (B) The mean percentage of wild-type activity detected in each region of the brain.

IDUA activity was detected in all sections of the brain, including hippocampus, striatum, cortex and cerebellum (FIG. 1A). Approximately 0.05-0.5 nmol/hr/mg tissue (0.83-8.3 mU/g tissue) of IDUA activity was detected in most brain regions corresponding to between 4.9% and 27% of the activity detected in wild-type animals (FIG. 1B). As it has been demonstrated that only a small fraction of enzymatic activity is necessary in order to provide functional and biochemical benefit (Ellinwood et al., 2007; Scott et al., 1993; Zheng et al., 2003), the results of this experiment are predicted to be well within the therapeutic range. The total percentage of the administered dose to reach the brain as detected by this assay was approximately 0.001%. This surprising and encouraging result demonstrates that intranasal IDUA rapidly reaches the brain from the nasal mucosa and likely does so by traveling along both the olfactory and trigeminal neural pathways as high levels of IDUA are observed in the trigeminal ganglion, the olfactory epithelium and olfactory bulb.

EXAMPLE II

Testing the Effectiveness of Enzyme Delivery to the CNS

The effectiveness of enzyme delivery to the CNS is described in the following examples, in which iduronidase enzyme was expressed in all sections of the brain after delivery of adeno-associated virus vector encoding human IDUA.

Figure 2:
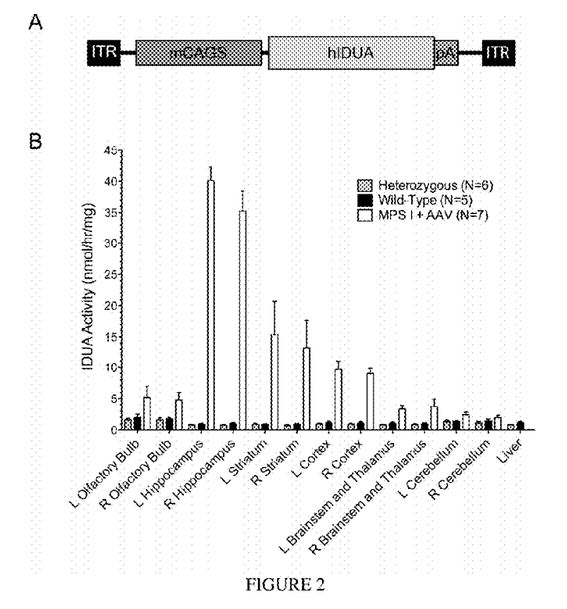
FIG. 2. ICV infusion of AAV8-MCI into neonates results in widespread high-level expression of IDUA (A) Depiction of the therapeutic AAV construct. AAV serotype 2 inverted terminal repeat (ITR) sequences flank the human IDUA cDNA regulated by a mini-CAGS (mCAGS) promoter. This construct was packaged using AAV serotype 8 capsids to produce AAV8-MCI. (B) Quantification of IDUA activity levels in microdissected brain samples 10 months post-infusion. Activity levels were determined by fluorometric enzyme assays using 4-umbelliferyl-iduronide substrate.

An AAV 2 based vector (AAV2-MCI) was constructed to contain the human IDUA (hIDUA) coding sequence under regulation of a strong mini-CAGS promoter (Ohlfest et al., 2005) (FIG. 2A). This vector was packaged at the University of Florida Vector Core using AAV 8 capsid protein, and $2 \times 10^{10}$ vector genomes was stereotactically infused into the right lateral ventricle of neonatal (4-6 day old) IDUA-deficient mice, anticipating that this route of administration would provide widespread distribution and vector-mediated hIDUA expression throughout the brain.

The animals were sacrificed at 10 months of age, and brain tissue was harvested by microdissection and homogenized. IDUA was undetectable in brain tissue extracts from IDUA-deficient controls. IDUA enzyme activity levels in extracts from treated animals exceeded levels detected from wild-type animals in all 12 microdissected regions of the brain studied (FIG. 2b). IDUA activity was the highest in brain structures within close proximity to the ventricles. Most notably, activity levels in the hippocampus were about 40-fold higher than wild-type levels. The striatum, cortex, brainstem, olfactory bulb, and cerebellum exhibited IDUA activity levels that were between 1.5- and 15-fold higher than wild-type levels. Although the AAV8-MCI vector was infused unilaterally into the right lateral ventricle, we did not observe a significant difference in IDUA activity levels between structures in the left and right hemispheres. Furthermore, IDUA activity was not detectable in the liver of treated animals, demonstrating that gene transfer was not systemic, but was confined largely to the CNS.

Figure 3:
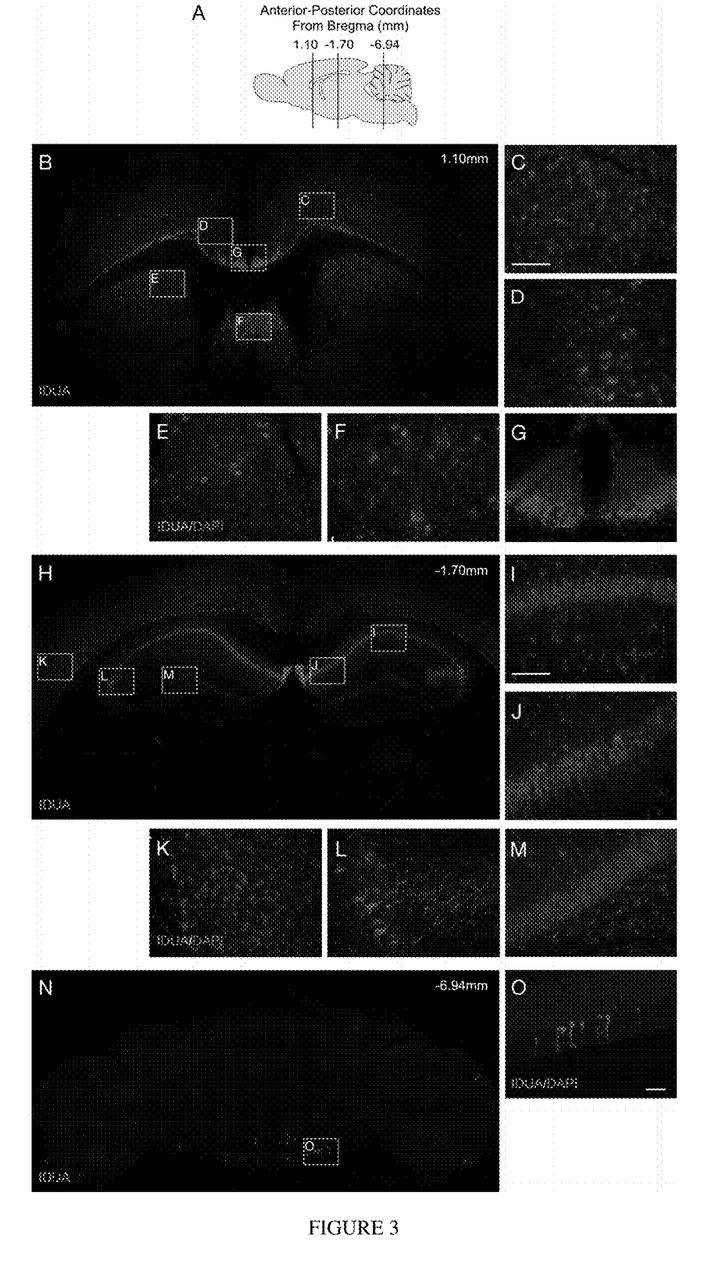

The distribution of hIDUA expression was investigated at the cellular level by immunofluorescence staining of histologic sections using an anti-hIDUA antibody. In coronal brain sections located at the anterior-posterior Bregma coordinates indicated in FIG. 3A, hIDUA staining was most intense in, although not limited to, structures within close proximity to the ventricular system (FIGS. 3B, H, and N). Medial to the lateral ventricles, hIDUA expression was visualized in the septal nucleus, and areas CA1, CA2, CA3, and dentate gyrus of the hippocampus (FIGS. 3F, I, J, L, and M). Dorsal to the lateral ventricles, expression was visualized in the corpus callosum and much of the cerebral cortex including the cingulate cortex (FIG. 3D) region of the limbic cortex. Additionally, the primary motor cortex (FIG. 3C), and entorhinal cortex (FIG. 3K) (regions involved in motor coordination, and learning and memory, respectively) stained positive for hIDUA dorsal to the lateral ventricles. Ventral to the lateral ventricles, positive staining was observed in the caudate putamen (FIG. 3E) and nucleus accumbens (not shown). The indusium griseum (FIG. 3G) and fasciola cinereum (not shown) are nuclei lining the 3rd ventricle that stained very intensely with the antibody. Furthermore, Purkinje neurons scattered throughout the cerebellum also stained positive for hIDUA, especially in areas immediately dorsal to the 4th ventricle (FIGS. 3N, O). In summary, hIDUA expression was observed at the cellular level in many structures involved in controlling learning and memory (limbic system) or motor function. Robust expression within these structures may be responsible for the resultant neurophenotype displayed by these animals described below.

Figure 4:
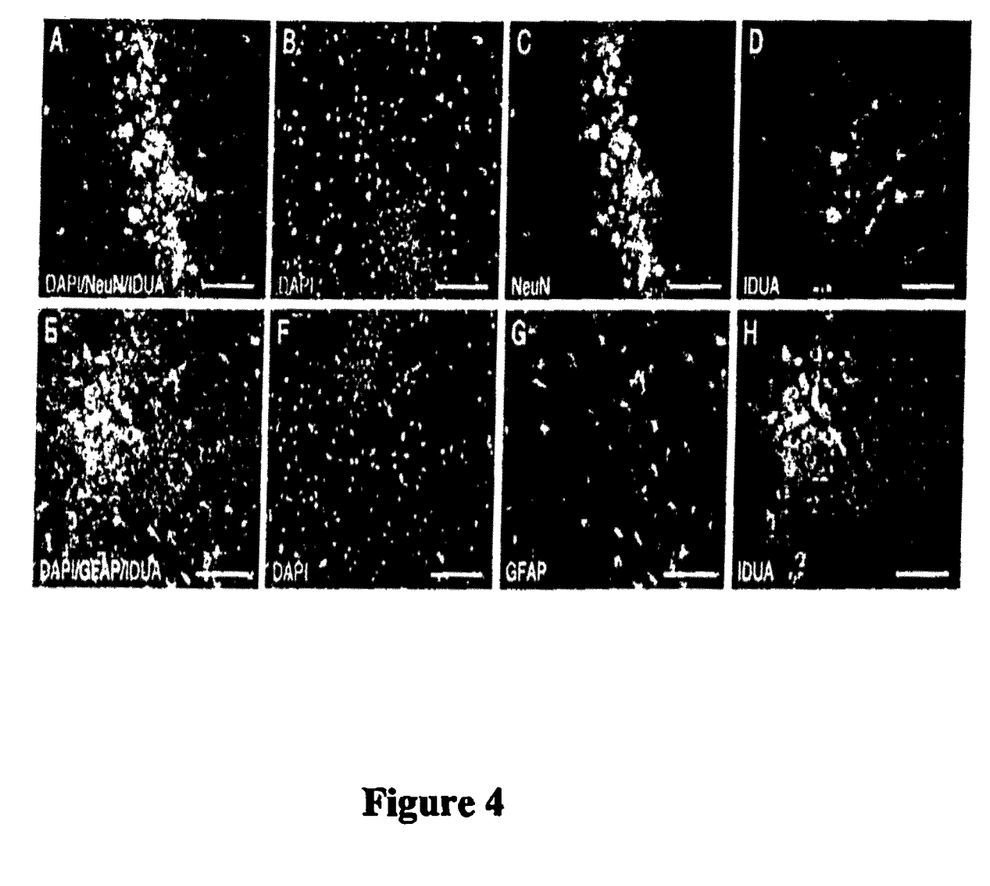
FIG. 4. IDUA is expressed primarily in neurons rather than in astrocytes. Cells expressing IDUA (red) displayed a strong co-localization with NeuN (green) resulting in yellow co-staining within pyramidal neurons of area CA3 of the hippocampus (A-D). However, in the same region of the brain, IDUA (red) did not co-localize with the astrocytic marker GFAP (green) (E-H). Scale bars are 100 ÿm in length.

In some cases, the type of cell staining positive for hIDUA expression was apparent from the morphologic structure revealed by the staining. For example, Purkinje cells in the cerebellum and pyramidal neurons within the hippocampus were easily identifiable by their characteristic morphology. By co-staining for hIDUA and for NeuN, we verified that much of the hIDUA staining observed in the brains of these animals was in neurons (FIGS. 4A-D), as previously reported after infusion of AAV8 vector into the brain (Blits et al., 2010; Broekman et al., 2006; Klein et al., 2006). However, co-staining of hIDUA with GFAP was not observed (FIGS. 4E-H), confirming that most of the hIDUA expression is from neuronal rather than astrocytic cells.

Figure 5:
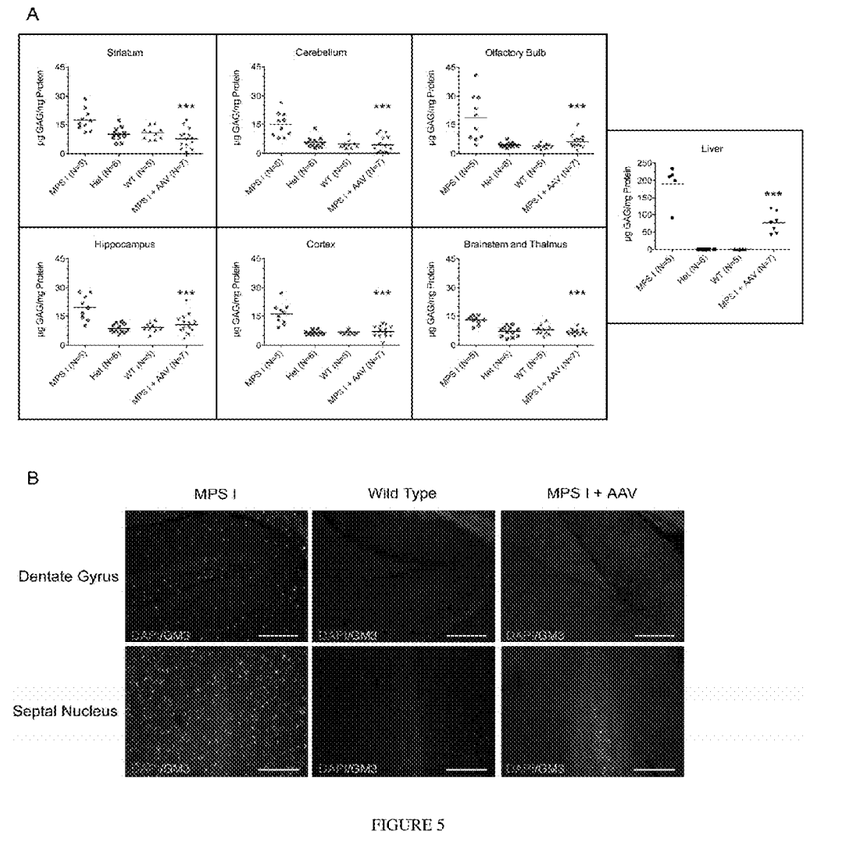

The widespread expression and distribution of hIDUA had a profound effect on accumulation of storage materials. Total GAG levels were elevated in untreated MPS I mice, but were normalized in the AAV8-treated mice throughout the brain, including the striatum, hippocampus, olfactory bulb, cerebral cortex, cerebellum, brainstem and thalamus, and were not significantly different from unaffected heterozygous or wild-type animals (FIG. 5A). Total GAG levels were reduced in the livers of AAV8-treated mice (perhaps due to enzymatic cross correction), although still significantly higher than observed in unaffected animals. Secondary accumulation of GM3 ganglioside was apparent in the brains of MPS I animals, as visualized by positive immunofluorescence staining within the white matter as well as in what appears to be punctate aggregates within grey matter throughout the brain. In contrast, the brains of wild-type and AAV8-MCI treated animals displayed GM3 ganglioside only within white matter (FIG. 5B).

Figure 6:
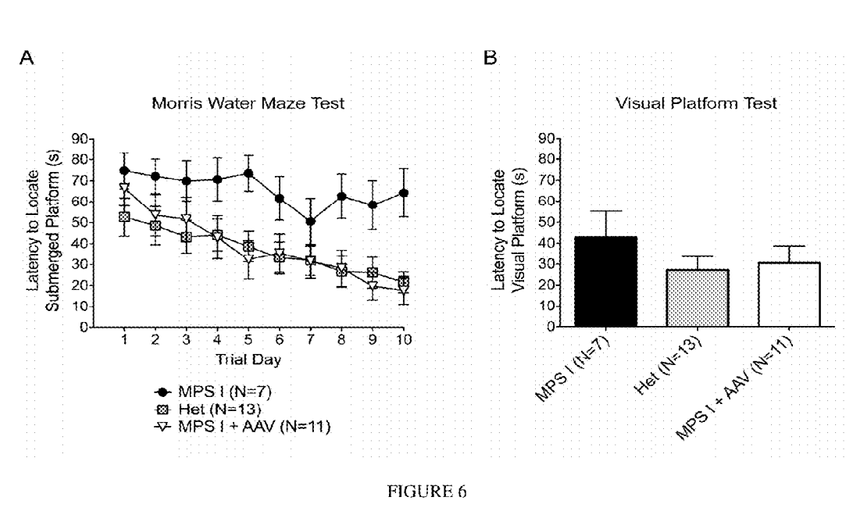
FIG. 6. A spatial learning and memory phenotype displayed by MPS I mice is completely prevented in MPS I mice treated by ICV infusion of AAV8-MCI as neonates. (A) Results of a modified Morris water maze task. MPS I mice displayed a significant deficit in their ability to locate a submerged platform compared to unaffected heterozygous mice (P<0.001). MPS I mice treated with AAV8-MCI performed equivalent to heterozygous mice (P<0.005 vs. MPS I mice). (B) To confirm that the deficit displayed by MPS I mice was not due to impaired vision caused by corneal clouding or to musculoskeletal or cardiopulmonary abnormalities, the mice were subjected to a visual platform test. No significant difference was observed in this task between any of the groups of animals.

Severe MPS1 in humans is associated with profound neurologic deficiency that is recapitulated in IDUA-deficient mice (Hartung et al., 2004; Pan et al., 2008; Reolon et al., 2006). To assess the extent to which the widespread distribution of hIDUA expression and associated reduction in storage material affected neurobehavior, a modified Morris water maze was employed as a test of spatial navigation and memory. In this test, animals were evaluated for the amount of time it takes to locate a submerged platform in a tank of water using three-dimensional visual cues positioned on the side of the tank. Prior to sacrificing the animals at 5 months of age, they were subjected to 4 trials of this test per day for a 10-day duration. Unaffected heterozygous littermates exhibited improved performance in this test, requiring an average of 20 seconds to find the submerged platform at the end of the 10-day testing period. In contrast, untreated MPS I mice displayed a significant deficit in locating the submerge platform in the northwest quadrant of the maze (**$P<0.005$ by repeated measures two-way ANOVA) (FIGS. 6A,B). Remarkably, complete prevention of this neurocognitive deficit was obtained in animals infused with AAV8-MCI at birth, as there was no statistical difference observed between these and unaffected heterozygous animals. On day 11 of the testing period, the submerged platform was moved to the northeast quadrant of the maze and a visual cue was placed directly on the platform. MPS I mice were able to locate the visible platform much faster than the submerged platform and did not perform significantly different than unaffected animals, demonstrating that the observed phenotype was neurocognitive in nature and not the result of impaired vision, or musculoskeletal or cardiopulmonary dysfunction in the MPS I animals. Herati et al. (2008) reported that IDUA activity in the brains of MPS I mice was reduced approximately 1000 fold from 1.0 nmol/hr/mg in normal mice to 0.001 nmol/hr/mg in MPS I mice. Approximately 0.05-0.5 nmol/hr/mg tissue was observed in the brain following intranasal administration of concentrated Aldurazyme which is about 5% to about 50% of normal amounts of IDUA activity.

In summary, neonatal ICV infusion of AAV8 vector was highly effective in achieving wide-spread, long-term, high-level hIDUA expression in the brains of MPS I mice that prevented accumulation of storage materials and emergence of neurocognitive deficit. Rapid distribution of IDUA to all parts of the brain of MPS 1 mice was demonstrated after intranasal administration of the enzyme protein. This treatment may also prevent the accumulation of storage materials in the brains of these animals as well as the emergence of neurocognitive deficiency, assessed as described above for MPS 1 mice treated by ICV infusion of AAV-IDUA vector at birth.

References

Al-Ghananeem et al., *AAPS Pharm. Sci. Tech.*, 3:E5 (2002).
Bagger et al., *Eur. J. Pharm. Sci.*, 21:235-242 (2004b).
Bagger et al., *Int. J. Pharm.*, 269:311-322 (2004a).
Baker et al., *Exp. Brain Res.*, 63:461 (1986).
Balin et al., *J. Comp. Neurol.*, 251:260-280 (1986).
Banks et al., *J. Drug Target*, 17:91-97 (2009).
Banks et al., *J. Pharmacol. Exp. Ther.*, 309:469 (2004).
Banks, *Biopolymers*, 90:589 (2008).
Barakat et al., *J. Pharm. Pharmacol.*, 58:63 (2006).
Baumgartner et al., *Neuron.*, 58:639 (2008).
Benedict et al., *Neuroendocrinology*, 86:136 (2007b).
Benedict et al., *Neuropsychopharmacology*, 32:239 (2007a).
Benedict et al., *Psychoneuroendocrinology*, 29:1326 (2004).
Bjoraker et al., *J. Dev. Behav. Ped.*, 27:290 (2006).
Blits et al., *J. Neuros. Methods*, 185:257 (2010).
Born et al., *Nat. Neurosci.*, 5:514 (2002).
Boulton et al., *Am. J. Physiol.*, 276:R818 (1999).
Boulton et al., *Neuropathol. Appl. Neurobiol.*, 22:325 (1996).
Bradbury et al., *Am. J. Physiol.*, 240:F329 (1981).
Bradbury et al., *J. Physiol.*, 339:519 (1983).
Brady, *Ann. Rev. Med.*, 57:283 (2006).
Broadwell et al., *J. Comp. Neurol.*, 242:632 (1985).
Broekman et al., *Neuroscience*, 138:501 (2006).
Buck, In: Kandel E R, Schwartz J H, Jessell T M, editors. Principles of neural science. 4th edition. New York: McGraw-Hill Companies. pp. 625-652 (2000).
Buxer et al., *J. Neurochem.*, 56:1012 (1991).
Cai et al., *Sichuan Da Xue Xue Bao Yi Xue Ban*, 39:438 (2008).
Capsoni et al., *Proc. Natl. Acad. Sci. USA*, 99:12432 (2002).
Carare et al., *Neuropathol. Appl. Neurobiol.*, 34:131 (2008).
Cauna, In: Proctor D F, Andersen I, editors. Amsterdam: Elsevier Biomedical Press. pp. 45-69 (1982).
Charlton et al., *Int. J. Pharm.*, 338:94 (2007b).
Charlton et al., *J. Drug Target*, 15:370 (2007a).
Charlton et al., *Pharm. Res.*, 25:1531 (2008).
Chen et al., *J. Alzheimers Dis.*, 1:35 (1998).
Chen et al., *J. Pharm. Sci.*, 95:1364 (2006).
Chow et al., *J. Pharm. Sci.*, 88:754 (1999).
Chow et al., *J. Pharm. Sci.*, 90:1729 (2001).
Clerico et al., In: Doty R L, editor. Handbook of olfaction and gustation. 2nd edition. New York: Marcel Dekker, Inc. pp. 1-16 (2003).
Costantino et al., *Int. J. Pharm.*, 337:1 (2007).
Cserr et al., *Am. J. Physiol.*, 240:F319 (1981).
Cserr et al., *Brain Pathol.*, 2:269 (1992).
Dahlin et al., *Eur. J. Pharm. Sci.*, 14:75 (2001).
Danhof et al., American Association of Pharmaceutical Scientists Annual Meeting, Atlanta, Ga. (2008).
Danielyan et al., *Eur. J. Cell. Biol.*, 88:315 (2009).
Davis et al., *Clin. Pharmacokinet.*, 42:1107 (2003).
de Lorenzo, In: Wolstenholme G E W, Knight J, editors. Taste and smell in vertebrates. London: Churchill. pp. 151-175 (1970).
De Rosa et al., *Proc. Natl. Acad. Sci. USA*, 102:3811 (2005).
DeSesso, *Qual. Assur.*, 2:213 (1993).
deSouza et al., *Eur. Neuropsychopharmacol.*, 19:53 (2009).
Dhanda et al., *Drug Del. Tech.*, 5:64 (2005).
Dhuria et al., *J. Pharm. Sci.*, 98:2501 (2009b).
Dhuria et al., *J. Pharmaceutical Sciences*, 99:1654 (2010).
Dhuria et al., *J. Pharmacol. Exp. Ther.*, 328:312 (2009a).
Diano et al., *J. Clin. Invest.*, 118:26 (2008).
Dickson et al., *Mol. Gen. Metab.*, 91:61 (2007).
Djupesland et al., *Laryngoscope*, 116:466 (2006).
Domes et al., *Biol. Psychiatry*, 61:731 (2007b).
Domes et al., *Biol. Psychiatry*, 62:1187 (2007a).
Dufes et al., *Int. J. Pharm.*, 255:87 (2003).
Einer-Jensen et al., *Exp. Brain Res.*, 130:216 (2000b).
Einer-Jensen et al., *Pharmacol. Toxicol.*, 87:276 (2000a).
Einer-Jensen et al., *Reproduction*, 129:9 (2005).
Ellinwood et al., *Mol. Genet. Metab.*, 91:239 (2007).
Fehm et al., *J. Clin. Endocrinol. Metab.*, 86:1144 (2001).
Field et al., *J. Neurocytol.*, 32:317 (2003).
Fliedner et al., *Endocrinology.*, 17:2088 (2006).
Francis et al., *Brain*, 131:3311 (2008).
Fratantoni et al., *Science*, 162:570 (1968).
Frey et al., *Drug Delivery*, 4:87 (1997).
Frey II, *Drug Del. Tech.*, 2:46 (2002).
Fuss et al., *Eur. J. Neurosci.*, 22:2649 (2005).
Gao et al., *Biomaterials*, 27:3482 (2006).
Gao et al., *Int. J. Pharm.*, 340:207 (2007a).
Gao et al., *J. Control Release*, 121:156 (2007b).
Gopinath et al., *Current Ther. Res.*, 23:596 (1978).
Gozes et al., *Curr. Alzheimer Res.*, 4:507 (2007).
Graff et al., *Pharm. Res.*, 20:1225 (2003).
Graff et al., *Pharm. Res.*, 22:235 (2005a).
Graff et al., *Pharm. Res.*, 22:86 (2005b).
Gray, 15th revised edition (Classic Collectors edition). New York: Bounty Books (1978).
Grevers et al., *Arch. Otorhinolaryngol.*, 244:55 (1987).
Groothuis et al., *J. Cereb. Blood Flow Metab.*, 27:43 (2007).
Gross et al., *J. Anat.*, 135:83 (1982).
Guastella et al., *Biol. Psychiatry*, 63:3 (2008).
Hadaczek et al., *Mol. Ther.*, 14:69 (2006).
Hallschmid et al., *Regul. Pept.*, 149:79 (2008).
Han et al., *J. Mol. Med.*, 85:75 (2007).
Hanson et al., *BMC Neurosci.*, 9:S5 (2008).
Hanson et al., *Drug Del. Tech.*, 4:66 (2004).
Hanson et al., San Diego, Calif.: Society for Neuroscience (2007).
Hanson et al., In: EPO, editor. Biopharm and HealthPartners Research Foundation (2008).
Hartung et al., *J. Am. Soc. Gene Ther.*, 9:866 (2004).
Hashizume et al., *Neuro. Oncol.*, 10:112 (2008).
Hatterer et al., *Blood*, 107:806 (2006).
Herati et al., *J. Gene Med.*, 10:972 (2008).
Hess et al., *Exp. Neuro.*, 186:134 (2004).
Horvat et al., *Eur. J. Pharm. Biopharm.*, 72:252 (2009).
Hussar et al., *Chem. Senses*, 27:7 (2002).
Illum, *J. Control Release*, 87:187 (2003).
Illum, *J. Pharm. Pharmacol.*, 56:3 (2004).
Itaya et al., *Brain Res.*, 398:397 (1986).
Jansson et al., *J. Drug Target*, 10:379 (2002).
Jogani et al., *Alzheimer Dis. Assoc. Disord.*, 22:116 (2008).
Johnston et al., *Cerebrospinal Fluid Res.*, 1:2 (2004).

Kakkis et al., *Mol. Gen. Met.*, 83:163 (2004).
Kandimalla et al., *J. Pharm. Sci.*, 94:613 (2005b).
Kandimalla et al., *Pharm. Res.*, 22:1121 (2005a).
Kida et al., *Neuropathol. Appl. Neurobiol.*, 19:480 (1993).
Kirsch et al., *J. Neurosci.*, 25:11489 (2005).
Klein et al., *J. Am. Soc. Gene Ther.*, 13:517 (2006).
Koos et al., *Neuroreport*, 16:1929 (2005).
Kosfeld et al., *Nature*, 435:673 (2005).
Kristensson et al., *Acta Neuropathol (Berl)*, 19:145 (1971).
Krivit, *Springer Seminars in Immunopathology*, 26:119 (2004).
Kumar et al., *Curr. Sci.*, 43:435 (1974).
Kumar et al., *Int. J. Pharm.*, 358:285 (2008).
Li et al., *Chin. J. Physiol.*, 48:7 (2005c).
Li et al., *Glia*, 52:245 (2005a).
Li et al., *J. Neurocytol.*, 34:343 (2005b).
Loftus et al., *Neuroscience*, 139:1061 (2006).
Luzzati et al., *J. Mol. Biol.*, 343:199 (2004).
Mackay-Sim, In: Doty R L, editor. Handbook of olfaction and gustation. 2nd edition. New York: Marcel Dekker, Inc. pp. 93-113 (2003).
Martinez et al., *Neuroscience*, 157:908 (2008).
Minn et al., *J. Drug Target*, 10:285 (2002).
Miragall et al., *J. Comp. Neurol.*, 341:433 (1994).
Muenzer, *J. Pediatrics*, 144:S27 (2004).
Munoz-Rojas et al., *Am. J. Med. Gen.*, 146A:2538 (2008).
Neufeld and Muenzer, In A. L. B. C. R. Scriver, W. S. Sly, et al (ed.), McGraw Hill, NY, pg. 3421 (2001).
Nonaka et al., *J. Pharmacol. Exp. Ther.*, 325:513 (2008).
Ohlfest et al., *Blood*, 105:2691 (2005).
Orchard et al., *J. Pediatrics*, 151:340 (2007).
Owens et al., *Diabet. Med.*, 20:886 (2003).
Pan et al., *Brain Res.*, 1188:241 (2008).
Pardridge, *NeuroRx*, 2:3 (2005).
Parker et al., *Psychoneuroendocrinology*, 30:924 (2005).
Pastores, *Exp. Opin. Biol. Ther.*, 8:1003 (2008).
Perl et al., *Lancet*, 1:1028 (1987).
Peters et al., *Bone Marrow Transpl.*, 31:229 (2003).
Pollock et al., *J. Anat.*, 191:337 (1997).
Raghavan et al., *J. Laryngol. Otol.*, 114:456 (2000).
Reger et al., *J. Alzheimers Dis.*, 13:323 (2008a).
Reger et al., *Neurobiol. Aging*, 27:451 (2006).
Reger et al., *Neurology*, 70:440 (2008b).
Rennels et al., *Adv. Neurol.*, 52:431 (1990).
Rennels et al., *Brain Res.*, 326:47 (1985).
Reolon et al., *Brain Res.*, 1076:225 (2006).
Rimmele et al., *J. Neurosci.*, 29:38 (2009).
Ross et al., *J. Neuroimmunol.*, 151:66 (2004).
Ross et al., *Neurosci. Lett.*, 439: 30 (2008).
Sakane et al., *J. Pharm. Pharmacol.*, 46:378 (1994).
Sakane et al., *J. Pharm. Pharmacol.*, 47:379 (1995).
Sarkar, *Pharm. Res.*, 9:1 (1992).
Schaefer et al., *J. Comp. Neurol.*, 444:221 (2002).
Scheibe et al., *Arch. Otolaryngol. Head Neck Surg.*, 134:643 (2008).
Schley et al., *J. Theor. Biol.*, 238:962 (2006).
Schulz et al., *Endocrinology*, 145:2696 (2004).
Scott et al., *Am. J. Hum. Genet.*, 53:973 (1993).
Shimizu et al., *Int. J. Obes. (Lond)*, 29:858 (2005).
Shipley, *Brain Res. Bull.*, 15:129 (1985).
Skipor et al., *Reprod. Biol.*, 3:143 (2003).
Steen et al., *J. Alzheimers Dis.*, 7:63 (2005).
Stefanczyk-Krzymowska et al., *Exp. Physiol.*, 85:801 (2000).
Takano et al., *J. Histochem. Cytochem.*, 53:611 (2005).
Thorne et al., *Brain Res.*, 692:278 (1995).
Thorne et al., *Clin. Pharmacokinet.*, 40:907 (2001).
Thorne et al., *Neuroscience*, 127:481 (2004).
Thorne et al., *Neuroscience*, 152:785 (2008).
Thorne, R G. 2002. The nasal pathways for drug delivery to the central nervous system: Studies with protein tracers and therapeutics. Doctoral Dissertation, University of Minnesota.
Unger et al., *J. Neuropath. Exp. Neuro.*, 52:460 (1993).
van den Berg et al., *Eur. J. Pharm. Biopharm.*, 58:131 (2004b).
Van den Berg et al., *J. Drug Target*, 11:325 (2003).
van den Berg et al., *J. Neurosci. Methods*, 116:99 (2002).
van den Berg et al., *Pharm. Res.*, 21:799 (2004a).
Van Diest et al., *J. Anat.*, 128:293 (1979).
Vyas et al., *AAPS PharmSciTech.*, 7:E1 (2006c).
Vyas et al., *Crit. Rev. Ther. Drug Carrier Syst.*, 23:319 (2006b).
Vyas et al., *J. Drug Target*, 13:317 (2005).
Vyas et al., *J. Pharm. Sci.*, 95:570 (2006a).
Walter et al., *Arch. Histol. Cytol.*, 69:37 (2006a).
Walter et al., *Neuropathol. Appl. Neurobiol.*, 32:388 (2006b).
Wang et al., *Cancer Chemother. Pharmacol.*, 57:97 (2006a).
Wang et al., *Eur. J. Pharm. Biopharm.*, 70:735 (2008).
Wang et al., *Int. J. Pharm.*, 317:40 (2006b).
Wang et al., *Int. J. Pharm.*, 341:20 (2007).
Weller et al., *Neurol. Res.*, 25:611 (2003).
Westin et al., *Eur. J. Pharm. Sci.*, 24:565 (2005).
Westin et al., *Pharm. Res.*, 23:565 (2006).
Williams et al., *J. Comp. Neurol.*, 470:50 (2004).
Wioland et al., *J. Histochem. Cytochem.*, 48:1215 (2000).
Xu et al., *J. Clin. Invest.*, 118:272 (2008).
Yamada et al., *Am. J. Physiol.*, 261:H1197 (1991).
Yang et al., *J. Pharm. Sci.*, 94:1577 (2005).
Zhang et al., *Acta Neuropathol. (Berl)*, 83:233 (1992).
Zhang et al., *Acta Pharmacol. Sin.*, 25:522 (2004a).
Zhang et al., *Int. J. Pharm.*, 275:85 (2004b).
Zhang et al., *J. Drug Target*, 14:281 (2006).
Zhao et al., *Acta Pharmacol. Sin.*, 28:273 (2007).
Zhao et al., *Chin. Med. Sci. J.*, 19:257 (2004).
Zheng et al., *Mol. Genet. Metab.*, 79:233 (2003).
Ziegler and Shapiro, In J. Donders and S. Hunter (ed.), Cambridge University Press, p. 427 (2007).

All publications, patents and patent applications are incorporated herein by reference. While in the foregoing specification, this invention has been described in relation to certain preferred embodiments thereof, and many details have been set forth for purposes of illustration, it will be apparent to those skilled in the art that the invention is susceptible to additional embodiments and that certain of the details herein may be varied considerably without departing from the basic principles of the invention.

What is claimed is:

1. A method for treating or inhibiting one or more neurological signs or symptoms associated with a mucopolysaccharidosis in a mammal in need thereof, comprising:
   intranasally administering an effective amount of an enzyme composition comprising alpha-L-iduronidase, iduronate-2-sulfatase, N-acetyl-alpha-D-glucosaminidase, betagalactosidase, or beta-glucuronidase.

2. The method of claim 1 wherein the administration inhibits neurological degeneration.

3. The method of claim 1 wherein the enzyme is alpha-L-iduronidase.

4. The method of claim 1 wherein the mammal is a human.

5. The method of claim 1 wherein the mucopolysaccharidosis is related to a deficiency in alpha-L-iduronidase.

6. The method of claim 1 wherein the mucopolysaccharidosis is a mucopolysaccharide type I disorder, a mucopolysaccharidosis type II disorder, or a mucopolysaccharidosis type VII disorder.

7. The method of claim 1 wherein multiple doses are administered.

8. The method of claim 1 wherein the composition is administered weekly.

9. The method of claim 1 wherein the composition is administered daily.

10. The method of claim 1 wherein the pH of the composition is about 4 to about 9.

11. The method of claim 1 wherein the pH of the composition is about 5 to about 7.

12. The method of claim 1 wherein about 200 to about 400 µL of the composition is administered.

13. The method of claim 1 wherein the concentration of the enzyme in the composition is about 5 mg/mL to about 25 mg/mL.

14. The method of claim 1 wherein about 1 to about 7 mg of the enzyme is administered.

15. The method of claim 1 wherein the administration treats neurological degeneration.

16. The method of claim 1 wherein the composition is administered to the upper one third of the nasal cavity.

17. The method of claim 1 wherein the composition does not include a permeation enhancer.

* * * * *

UNITED STATES PATENT AND TRADEMARK OFFICE
CERTIFICATE OF CORRECTION

PATENT NO.        : 8,609,088 B2
APPLICATION NO.   : 13/465575
DATED             : December 17, 2013
INVENTOR(S)       : Wolf et al.

It is certified that error appears in the above-identified patent and that said Letters Patent is hereby corrected as shown below:

On the title page, in column 2, under "Other Publications", line 14, delete "V," and insert --V.,--, therefor In the Specification In Column 1, line 6-7, before "Cross-Reference to Related Applications", insert --Statement of Government Rights
This invention was made with government support under P01-HD032652 awarded by the National Institutes of Health. The government has certain rights in the invention.¶--, therefor In column 2, line 30, delete "intracerebrovectricular" and insert --intracerebroventricular--, therefor In column 5, line 59, delete "CA3of" and insert --CA3 of--, therefor In column 8, line 47, delete "2005a)" and insert --2005a--, therefor In column 9, line 52, delete "2004)," and insert --2004).--, therefor In column 11, line 7, delete "2004a)" and insert --2004a--, therefor In column 11, line 66, delete "Al" and insert --A1--, therefor

In column 12, line 15, delete "(1991)" and insert --(1991))--, therefor

In column 17, line 51, delete "cm3" and insert --$cm^3$--, therefor

In column 20, line 44, delete "6A,B" and insert --6A, B--, therefor

In column 20, line 56, after "animals.", insert --¶--, therefor

Signed and Sealed this
Sixteenth Day of September, 2014

Michelle K. Lee
*Deputy Director of the United States Patent and Trademark Office*